United States Patent
Burton et al.

(10) Patent No.: US 7,723,335 B2
(45) Date of Patent: May 25, 2010

(54) TRIAZINE COMPOUNDS AND THEIR USE IN FORMING MULTIDIMENSIONAL LIBRARIES FOR AFFINITY CHROMATOGRAPHY

(75) Inventors: Steven James Burton, Cambridge (GB); Abid Hussain, Cambridge (GB); James Christopher Pearson, Cambridge (GB)

(73) Assignee: Prometic Biosciences Ltd. (IM)

( * ) Notice: Subject to any disclaimer, the term of this patent is extended or adjusted under 35 U.S.C. 154(b) by 165 days.

(21) Appl. No.: 10/536,953

(22) PCT Filed: Dec. 9, 2003

(86) PCT No.: PCT/GB03/05368

§ 371 (c)(1),
(2), (4) Date: Aug. 8, 2005

(87) PCT Pub. No.: WO2004/052870

PCT Pub. Date: Jun. 24, 2004

(65) Prior Publication Data

US 2006/0052598 A1  Mar. 9, 2006

Related U.S. Application Data

(60) Provisional application No. 60/443,092, filed on Jan. 28, 2003.

(30) Foreign Application Priority Data

Dec. 9, 2002 (GB) ................... 0228724.1

(51) Int. Cl.
C07D 403/14 (2006.01)
C07D 251/70 (2006.01)
C07D 251/54 (2006.01)
A61K 31/53 (2006.01)
B01D 15/08 (2006.01)
G01N 33/48 (2006.01)

(52) U.S. Cl. ................... 514/245; 544/198; 544/207

(58) Field of Classification Search ............ 544/198, 544/207; 514/245
See application file for complete search history.

(56) References Cited

U.S. PATENT DOCUMENTS

| 4,731,393 A | 3/1988 | Hofmann et al. |
| 6,248,710 B1 | 6/2001 | Bijsterbosch et al. |
| 6,482,255 B1 | 11/2002 | Lavery et al. |

FOREIGN PATENT DOCUMENTS

| EP | 0122458 | 10/1984 |
| EP | 0542374 | 5/1993 |
| EP | 1319643 | 6/2003 |
| GB | 2053926 | 2/1981 |
| GB | 2149808 | 6/1985 |
| JP | 61-500299 | 2/1986 |
| WO | WO 84/04329 | 11/1984 |
| WO | WO 97/10887 | 3/1997 |
| WO | WO 00/67900 | 11/2000 |
| WO | WO 01/42228 | 6/2001 |

OTHER PUBLICATIONS

Löwik, D.W.P.M et al. "Synthesis of Macrocyclic, Triazine-Based Receptor Molecules" *European Journal of Organic Chemistry*, 2001, pp. 2825-2839, vol. 2001, No. 15.

Zhang, W. et al. "Orthogonal Convergent Synthesis of Dendrimers Based on Melamine with One or Two Unique Surface Sites for Manipulation" *Journal for the American Chemical Society*, 2001, p. 8914-8922, vol. 123, No. 37.

Zhang, W. et al. "Synthesis and Characterization of Higher Generation Dendrons Based on Melamine Using P-Aminobenzylamine. Evidence for Molecular Recognition of Cu(II)" *Tetrahedron Letters*, Aug. 6, 2001, pp. 5355-5357, vol. 42, No. 32.

*Primary Examiner*—Venkataraman Balasubramanian
(74) *Attorney, Agent, or Firm*—Saliwanchik, Lloyd & Saliwanchik

(57) ABSTRACT

A compound of the formula (I) wherein each Z is the same or different and is formula (a) or —Y wherein each X is the same or different and is a multivalent aminyl group or diaminyl-terminated spacer; each Y is the same or different aminyl group; and M is a support matrix.

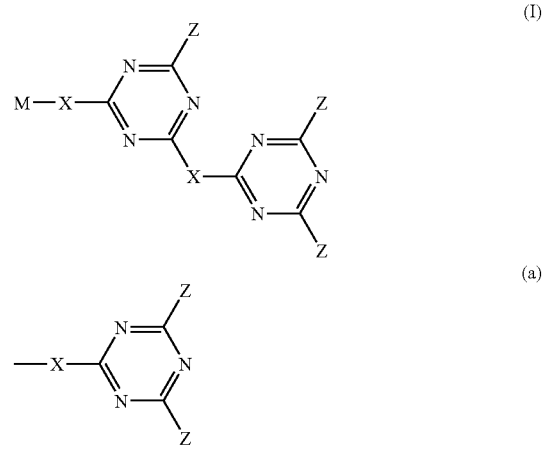

15 Claims, No Drawings

TRIAZINE COMPOUNDS AND THEIR USE IN FORMING MULTIDIMENSIONAL LIBRARIES FOR AFFINITY CHROMATOGRAPHY

This application is a National Stage Application of International Application Number PCT/GB2003/005368, filed Dec. 9, 2003; which claims priority to Great Britain Application No. 0228724.1, filed Dec. 9, 2002 and U.S. Provisional Application No. 60/443,092, filed Jan. 28, 2003.

FIELD OF THE INVENTION

This invention relates to triazine compounds and to their use in forming multi-dimensional affinity ligand libraries, and also to the attachment of affinity ligands to matrices. The invention further relates to the use of the ligands for the purification of natural, recombinant or transgenic proteinaceous materials. The ligands may be also used in medical devices and as therapeutic drugs.

BACKGROUND OF THE INVENTION

The principle of affinity chromatography is based on the phenomenon of molecular recognition. A ligand immobilised on a support matrix is able to form a specific, reversible interaction with a target molecule in the presence of a mixture of other molecules. The nature of the interaction may be hydrogen-bonding, electrostatic forces, stacking as a result of favourable geometry or any other aspect that encourages the host-target relationship. Once bound to the target, the ligand-target interaction should be sufficiently strong to allow the removal of the other contaminant molecules from a mixture while keeping the ligand-target complex intact. However, the binding must be sufficiently weak such that an induced change in local, e.g. buffer conditions causes disruption to the interaction, thus releasing the target molecule in its now purified form. The immobilised ligand, now devoid of protein, can be used again for a subsequent purification. Desirable properties of an affinity ligand include chemical and thermal stability, and high selectivity.

The ligand may be designed to fit a particular target molecule by use of molecular modelling or it may be selected by screeing combinatorial libraries. The combinatorial approach affords a large number of ligands which may be constructed to incorporate a variety of chemical moieties including hydrophilic, hydrophobic, charged or neutral groups or a mixture thereof. Combinatorial libraries may conveniently be synthesised by incorporating commercially available compounds, including amino acids, carboxylic acids and amines, in a step-wise synthesis directly on the surface of the support matrix. Alternatively, the ligand may be synthesised and subsequently attached to a support matrix.

Cyanuric chloride, or 2,4,6-trichlorotriazine (hereinafter referred to as triazine), is a symmetrical molecule. 2,4,6-Trisubstituted triazines can readily be generated by reaction of cyanuric chloride with nucleophiles such as amine compounds. Triazine derivatives are useful as adsorbents and for other purposes; see WO-A-97/10887 and WO-A-00/67900.

Affinity ligand libraries may be built up on a hydroxylic support such as cross-linked agarose. To date, all triazine-based ligand libraries built up on agarose have comprised a support with a single substituted triazine component (see WO-A-97/10887) or with macrocyclic rings incorporating triazine groups (see WO-A-01/42228).

SUMMARY OF THE INVENTION

The present invention is based at least in part on the discovery that useful affinity libraries can be obtained by combining two or more triazine rings into a single ligand structure, to provide larger ligands, with increased chemical diversity and enhanced selectivity compared to ligands based on single triazine rings.

According to the present invention, a novel compound has formula I

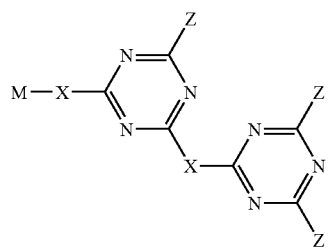

wherein each Z is the same or different and is

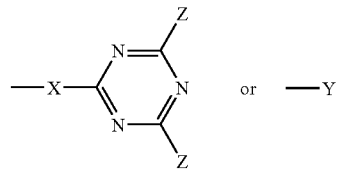

wherein each X is the same or different and is a multivalent (including divalent) aminyl group or diaminyl-terminated spacer;
each Y is the same or different aminyl group; and
M is a support matrix.
Another aspect of this invention is compounds of the formula

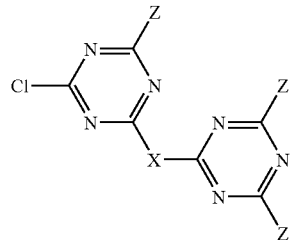

wherein Z is as defined above. This compound may be reacted with a support M having a suitable functional group.

Typically, a compound of the invention is made by the sequential reaction of a matrix-immobilised amine with cyanuric chloride, an aminyl group Y, a diamine X, cyanuric chloride, a second aminyl group Y and a third aminyl group. More generally, by the iterative addition of a spacer (X) followed by a triazine nucleus it is possible to construct ligands having a chain of alternating spacer-triazine groups. The chlorine atoms of any terminal triazine may be substituted by an amine which may itself be multi-functional, optionally with certain functionalities blocked by a protecting group to facilitate oriented attachment. The use of multi-functional amine spacer groups permits the construction of more elaborate ligands, leading to branched, antennary, tubular or globular structures. Further, a library of ligands may be produced, on common support M. This constitutes a further aspect of the invention.

Compounds of the invention are "multi-dimensional". The number of dimensions corresponds to the number of different groups Y.

A compound of the invention (which includes libraries) may be used for the separation, isolation, purification, characterisation, identification, quantification or discovery of peptides and proteins. In particular, it may be used for the separation, purification or discovery of a proteinaceous material, which comprises subjecting a sample containing the material to affinity chromatography. The proteinaceous material may be an immunoglobulin or a subclass, fragment, precursor or derivative thereof, including fusion proteins, whether derived from natural or recombinant sources. Further, a compound of the invention may be used for the removal of contaminants, including toxic or pathogenic entities, from a preparation of biological or pharmaceutical compound. It may also be used for drug discovery.

DESCRIPTION OF THE INVENTION

The support material M may be any suitable compound or material, particulate or non-particulate, soluble or insoluble, porous or non-porous. In conjunction with an affinity legend, as defined, it provides a convenient means of separating affinity legends from solutes in a solution brought into contact therewith.

In order to prepare a compound of the invention, a support material such as agarose is subjected to controlled reaction with an activating agent such as epichlorohydrin to introduce reactive groups which facilitate the attachment of an amine group or spacer X. The amount of reactive groups introduced can be measured by suitable assay and expressed in units of μmol/g of settled gel. Excess solvent may be removed by suction or filtration under gravity prior to attachment of an amine spacer group. The activated agarose may be first reacted with an amine that provides a spacer (X).

Minimally, X is divalent and linking. When linking M to a triazine, it must be at least divalent with those valencies being amine-containing. Similarly, when X links two triazines, it is at least divalent and those valencies must be amine-containing. Typically, X is initially at least either monovalent, such as ammonia, divalent, such as 1,2-diaminoethane or trivalent, such as diethylenetriamine or tris(aminoethyl)amine. It will be appreciated nevertheless that X may be substituted by groups such as hydroxyl, without losing its function, and this within the scope of the invention.

Examples of the product of this first reaction are shown in formulae II, III, IV and V

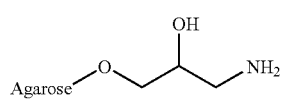

II

-continued

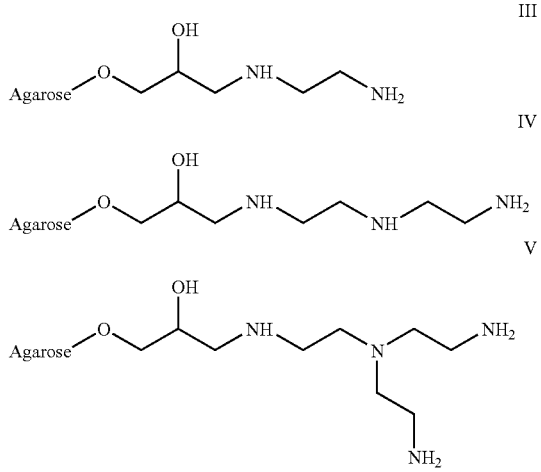

The number of amino groups introduced can be determined by any suitable assay, such as TNBS, and may be expressed as μmol amine/g of settled gel. Each of the aliphatic amines introduced at this stage is next reacted with cyanuric chloride. For example, a compound of formula II is reacted to generate a triazine-activated agarose of formula VI

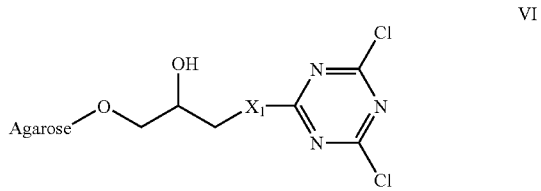

The total chloride content on the triazine activated resin may be measured as chloride ion following alkaline hydrolysis.

In order to prepare a 3D library, i.e. a compound containing 2 or more triazine groups and three independently available Y groups, one of the chlorine atoms is substituted by an amine $Y_1$. The second chlorine atom is replaced by a second spacer $(X_2)$ which may be a diamine, triamine or tetramine, of any chain length. $X_2$ may be divalent or trivalent (examples given above).

Each addition of an amine to the triazine ring results in the elimination of a chloride ion, which may be assayed. Results may be expressed in terms of μmol chloride ion released per gram of settled gel. If the result from the activation assay=A; the result from the amine assay=B; the result from a chloride assay where one chloride ion has been eliminated=C(i), then assuming 100% conversion of starting material to product:

$A=B=C(i)$ (μmol/g of settled gel)

When the second chloride ion, C(ii) has been eliminated, then:

$A=B=C(i)=C(ii)$; and $C(i)+(C(ii))=2A=2B$.

A second triazine substitution step generates a structure of formula VII

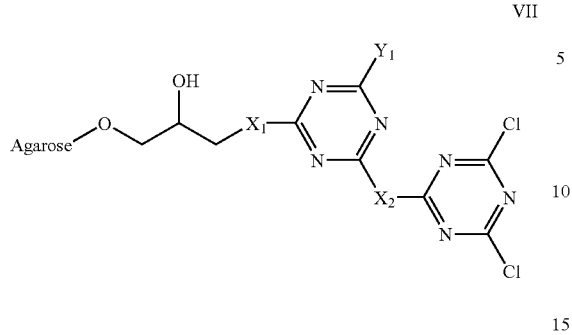

VII

In a 3D library, both chlorine atoms on the second triazine nucleus are substituted sequentially by amines $Y_2$ and $Y_3$ to give a product of formula VIII

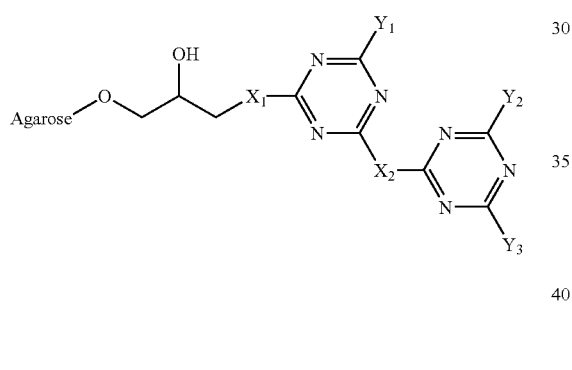

VIII

Examples of other structures built up from these building blocks are shown as formulae IX and X

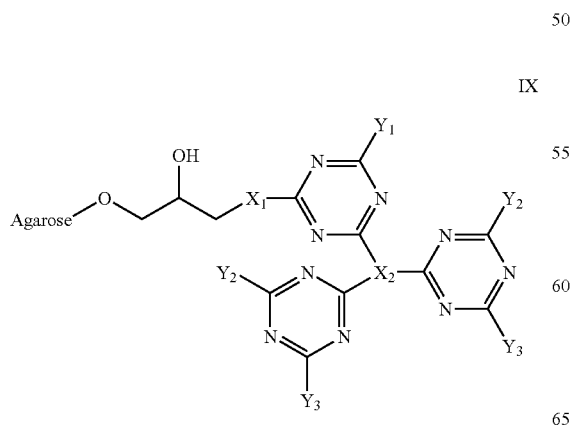

IX

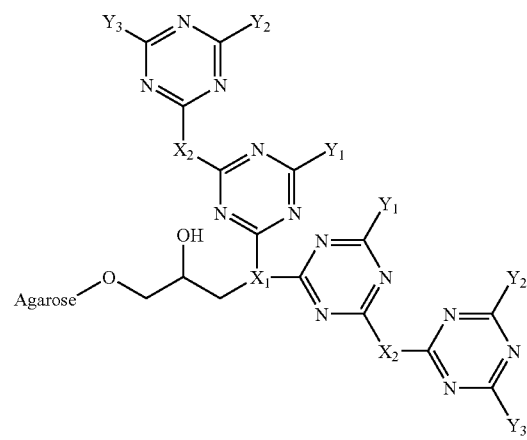

X

Alternating triazine and multivalent spacer groups allows the production of ligands with any number of independently variable amine substitution positions, as exemplified in formulae XI to XIII

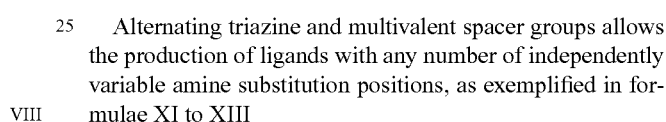

XI

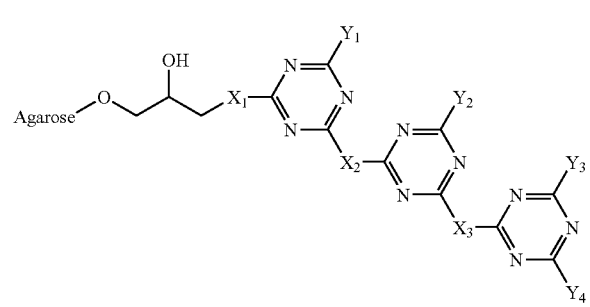

XII

-continued

XIII

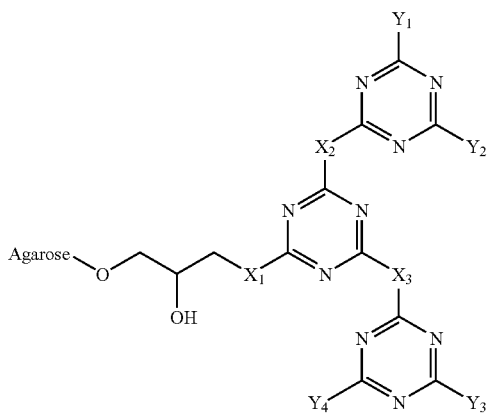

Formulae XI and XIII have different degrees of branching, but the same degree of dimensionality. This is in part because the additional branching in XIII is at X, i.e. two identical triazine rings are introduced at this point, rather than on a further triazine.

The following Examples illustrate the invention.

EXAMPLE 1

This Example illustrates the preparation of epoxide-activated PuraBead resin. PuraBead is a porous breaded agarose support which is cross-linked to aid durability.

Epoxide activation: A sample of PuraBead 6XL (333 g) was slurried in water (213 mL) and mixed with 10M NaOH (26.6 mL). The mixture was stirred using an overhead stirrer until a constant temperature of 34° C. was reached. Epichlorohydrin (24 mL) was added in two equal portions and the temperature was increased to 40° C. After 1 h, the slurry was filtered and washed with water (10×350 mL). Epoxide assay on the washed, activated resin indicated a substitution level of 23.3 μmol epoxide/g settled gel.

EXAMPLE 2

This Example illustrates the preparation of aminated gel from an epoxide-activated gel.

Amine activation: The epoxy-activated gel obtained in Example 1 (226 g) was slurried in water (180 mL) and treated with 0.88 ammonia (45 mL). The reaction mixture was left to stir overnight at 40° C. After this period, the gel was filtered and washed with water (10×500 mL) to obtain the amine activated resin (ca 220 g). TNBS assay on a portion of the gel showed the amine level was 23.2 μmol/g settled gel.

EXAMPLE 3

This Example illustrates the reaction of aminated resin with cyanuric chloride to give a dichlorotriazine-activated gel.

Triazine activation: The amine-activated gel (200 g) prepared in Example 2 was washed with 1.0 M potassium phosphate buffer (200 mL, pH 7). The settled gel was transferred to a beaker and mixed with water (50 mL) and 1.0M potassium phosphate buffer (50 mL, pH 7). The whole mixture was transferred to a 3-neck 1-litre round bottom flask. Vigorous stirring was maintained as acetone (100 mL) was added. The flask was cooled to a steady temperature of 0° C. A solution of cyanuric chloride (5 g) in cold acetone (50 mL) was added from the side arm. The reaction was stopped after 1 h and the flask contents were transferred to a sinter funnel. The dichlorotriazine gel was washed with 50% acetone (1 L), water (1 L), 50% acetone (1 L) and water (2 L) to give the triazine activated resin (ca. 200 g). A chloride assay determined that the total chloride ion content was 46 μmol/g settled gel.

EXAMPLE 4

This Example illustrates the addition of the first amine to the dichlorotriazine gel.

Substitution of $Y_1$: Dichlorotriazine gel (200 g) prepared in Example 3 was slurried in water (100 mL) and treated with a solution of β-alanine (0.2M) in water (100 mL) that had been basified with 10M NaOH (4 mL). The reaction vessel was shaken for 1 h at room temperature after which the contents were filtered and washed with 50% DMF (5×125 mL) and water (10×125 mL).

EXAMPLE 5

This Example illustrates the displacement at a higher temperature of the second chloride ion with a diamine spacer.

Second substitution to add the spacer $X_2$: The $Y_1$-substituted gel obtained in Example 4 was slurried in water (100 mL) and treated with a solution of ethylenediamine (0.4M) in water (100 mL). The reaction vessel was allowed to shake at 60° C. for 2 days. After cooling, the resultant gel was washed with 50% DMF (5×125 mL), water (5×125 mL), 0.1M HCl (5×125 mL), 30% isopropanol/0.2M NaOH (5×125 mL) and water (10×125 mL). A TNBS assay on a sample of the gel indicated an amine substitution of 26.7 μmol/g. A chloride assay on the supernatant indicated chloride release of 27.2 μmol/g.

Second Triazine Step: The procedure was identical to the first triazine activation step, as described in Example 3.

EXAMPLE 6

This Example illustrates the addition of the first amine to the second triazine ring.

Substitution of $Y_2$: The gel obtained from the second triazine coupling step in Example 5 was weighed into eight bottles (12.5 g in each bottle). The samples were slurried in 50% DMF (6.25 mL). Each bottle was then charged with a solution of the selected amine (0.2M, 6.25 mL). Amines containing carboxylate moieties or those obtained as hydrochloride salts were basified with the required volume of 10M NaOH to bring the overall pH to approx. 9-10. The samples were shaken at room temperature for 1 h.

Supernatants (100 mL) were removed from each bottle to assess the progress of the reaction by chloride ion assay. Table 1 shows the chloride release figures after the first amine substitution.

TABLE 1

| Column Index in final library | Intermediate Amine | Chloride release (μmol/g) |
|---|---|---|
| 1 | β-alanine | 15.61 |
| 2 | 3-aminobenzoic acid | 17.13 |
| 3 | 4-aminobenzoic acid | 9.83 |
| 4 | L-glutamic acid | 17.52 |
| 5 | DL-valine | 13.97 |
| 6 | 4-aminobutyric acid | 18.77 |
| 7 | L-tyrosine | 19.73 |
| 8 | 6-amino-n-caproic acid | 17.16 |

The eight intermediate gels were washed with 50% DMF (5×12.5 mL) and water (10×12.5 mL).

EXAMPLE 7

This Example illustrates the combinatorial addition of the final amine ($Y_3$) on the second triazine ring to give a library of 3D ligands according to Formula VIII Second substitution $Y_3$: This was afforded by a variation on the method adapted from the second spacer arm ($X_2$) substitution given in Example 5. The syntheses were preformed directly in microspin columns. Alternatively, a 96-well block may also be used.

Each of the eight intermediates (4.0 g) obtained in Example 6 was slurried in 0.4% Tween-20 (2 mL). A slurry of the first intermediate (0.375 mL) was dispensed down a row of eight wells (0.375 mL per well). The process was repeated for the second intermediate down the second row of wells and so on until all eight first stage intermediates had been dispensed down each respective row.

A solution of the first final stage amine ($Y_3$) (0.4M) in 50% DMF was dispensed across the first row (0.125 mL per well) until all eight wells had been charged. The procedure was repeated until all eight rows had been charged with the selected final stage amine ($Y_3$). Thus each well of the 8×8 array constitutes a different individual ligand structure.

Once the addition of $Y_3$ was complete, the library block was shaken in an oven at 60° C. for 2 days. Upon removal and cooling (1 h) the block was allowed to drain in to a deep well microtitre plate. The filtrate collected was assayed to determine the release of chloride ion, thus determining the extent of the reaction. The library block was washed with 50% DMF (2×1 ml), water (2×1 mL), 0.1 M HCl (2×1 ml), water (2×1 mL), 0.2M NaOH/30% isopropanol (2×1 mL), water (2×1 mL) and 20% ethanol (2×1 mL).

The results in Table 2 below show the chloride release data obtained after the second substitution ($Y_3$), reported as μmol chloride released per g gel.

TABLE 2

| | 1 | 2 | 3 | 4 | 5 | 6 | 7 | 8 |
|---|---|---|---|---|---|---|---|---|
| 4-(2-aminoethyl)morpholine | 13.32 | 16.68 | 15.75 | 16.68 | 16.45 | 15.07 | 16.33 | 12.8 |
| 1-(2-aminoethyl)piperidine | 14.29 | 17.40 | 14.62 | 15.52 | 15.75 | 15.98 | 16.92 | 14.29 |
| 3-aminobenzyl alcohol | 13.53 | 16.92 | 12.18 | 17.64 | 15.29 | 16.56 | 16.80 | 14.4 |
| Tyramine | 11.49 | 14.29 | 11.10 | 14.07 | 12.80 | 13.64 | 11.88 | 12.39 |
| 2-(p-tolyl)ethylamine | 13.43 | 16.80 | 15.63 | 18.63 | 17.16 | 16.68 | 15.41 | 15.75 |
| Benzylamine | 13.11 | 16.68 | 14.29 | 16.21 | 16.21 | 16.21 | 15.29 | 14.29 |
| Tryptamine | 16.68 | 20.95 | 19.90 | 21.08 | 21.35 | 20.29 | 26.74 | 19.39 |
| 1,5-diaminoheptane Dihydrochloride | 14.82 | 19.31 | 15.5 | 21.6 | 15.0 | 20.9 | 254.0 | 16.3 |

The resultant library was screened to test for binding activity/affinity against various target proteins. Table 3 below gives details of a screen performed on human plasma. First the ethanol preservative was washed out of each position in the library by adding 2 mL of 25 mM sodium phosphate pH7.0 to the top of the gel bed, and this was allowed to run through under gravity to displace the 20% ethanol preservative in the gel. Human plasma was diluted 1:20 (v/v) in phosphate buffered saline, 2 mL added to the top of each gel bed and allowed to run through under gravity. The flow through (FT) that ran off each library component was collected separately. Each gel bed was then washed to remove non-bound protein by the application of 2 mL sodium phosphate buffer pH7.0 in a similar manner; the wash fraction (W) that ran off each library component was collected separately. In the first of two elution steps (E1) designed to remove bound protein, 1 mL of 10 mM sodium phosphate/citric acid pH6.5 was added to the top of each gel bed and allowed to run through under gravity and collected separately. Next the second elution step (E2) was applied, designed to remove protein not released in the first elution step: 1 mL of 50 mM citric acid was added to the top of each gel bed and allowed to run through under gravity and collected separately. Finally a sanitisation step (San) was applied, designed to remove all remaining contaminating material on the gel: 1 mL of 0.2M sodium hydroxide/30% isopropanol was added to the top of each gel bed and allowed to run through under gravity and collected separately.

The protein released in each step was assayed in each of the collected elution fractions: FT, W, E1, E2 and San. The results are shown in Tables 3A-E.

Each fraction collected from the library is presented as a grid as per Table 2. The figures give the protein recovered from each library component in μg:

TABLE 3A

| FT | First Amine | | | | | | | |
|---|---|---|---|---|---|---|---|---|
| Second Amine | 1 | 2 | 3 | 4 | 5 | 6 | 7 | 8 |
| 9 | 20967 | 13050 | 13863 | 14722 | 9075 | 13050 | 13863 | 14722 |
| 10 | 17601 | 8546 | 7154 | 17601 | 18667 | 13050 | 12284 | 10880 |
| 11 | 18667 | 7587 | 9639 | 15630 | 7587 | 7587 | 9075 | 10240 |
| 12 | 17601 | 8546 | 12284 | 13863 | 11561 | 11561 | 9639 | 9075 |
| 13 | 15630 | 8050 | 9075 | 13050 | 8546 | 11561 | 9075 | 11561 |
| 14 | 17601 | 7154 | 10880 | 13050 | 14722 | 12284 | 10240 | 13050 |
| 15 | 18667 | 4572 | 10880 | 7154 | 6749 | 10880 | 5094 | 7587 |
| 16 | 18667 | 12284 | 8546 | 13050 | 14722 | 12284 | 15630 | 12284 |

TABLE 3B

| W | First Amine | | | | | | | |
|---|---|---|---|---|---|---|---|---|
| Second Amine | 1 | 2 | 3 | 4 | 5 | 6 | 7 | 8 |
| 9 | 740 | 885 | 809 | 740 | 927 | 846 | 971 | 809 |
| 10 | 774 | 846 | 809 | 1071 | 774 | 740 | 885 | 740 |
| 11 | 846 | 846 | 809 | 846 | 1071 | 740 | 971 | 774 |
| 12 | 927 | 927 | 809 | 971 | 971 | 774 | 1128 | 971 |
| 13 | 1019 | 971 | 971 | 971 | 1019 | 846 | 1128 | 1071 |
| 14 | 971 | 1071 | 1071 | 971 | 971 | 1071 | 1189 | 885 |
| 15 | 971 | 1326 | 1128 | 1128 | 1255 | 971 | 1403 | 1071 |
| 16 | 846 | 885 | 885 | 846 | 809 | 774 | 885 | 675 |

TABLE 3C

| E1 | First Amine | | | | | | | |
|---|---|---|---|---|---|---|---|---|
| Second Amine | 1 | 2 | 3 | 4 | 5 | 6 | 7 | 8 |
| 9 | 878 | 1727 | 1459 | 782 | 782 | 694 | 1544 | 828 |
| 10 | 464 | 1101 | 828 | 537 | 464 | 427 | 1101 | 574 |
| 11 | 1165 | 1930 | 1826 | 1165 | 1459 | 929 | 1826 | 1544 |
| 12 | 1727 | 2407 | 1826 | 1459 | 1727 | 1459 | 1930 | 1727 |
| 13 | 1633 | 2407 | 2041 | 1544 | 2041 | 1380 | 1826 | 1826 |
| 14 | 1165 | 2684 | 1930 | 1459 | 1633 | 1233 | 1826 | 1459 |
| 15 | 1930 | 2988 | 2684 | 1633 | 2407 | 1727 | 2041 | 2041 |
| 16 | 653 | 2041 | 1304 | 694 | 574 | 613 | 1233 | 694 |

TABLE 3D

| E2 | First Amine | | | | | | | |
|---|---|---|---|---|---|---|---|---|
| Second Amine | 1 | 2 | 3 | 4 | 5 | 6 | 7 | 8 |
| 9 | 25 | 178 | 25 | 25 | 0 | 0 | 79 | 25 |
| 10 | 0 | 25 | 0 | 0 | 0 | 0 | 0 | 25 |
| 11 | 129 | 904 | 599 | 225 | 270 | 79 | 519 | 225 |
| 12 | 225 | 1006 | 810 | 397 | 397 | 129 | 1614 | 519 |
| 13 | 313 | 1793 | 1531 | 397 | 856 | 225 | 2213 | 479 |
| 14 | 438 | 1531 | 954 | 397 | 558 | 313 | 1701 | 519 |
| 15 | 270 | 1793 | 1118 | 356 | 680 | 225 | 1453 | 479 |
| 16 | 0 | 129 | 25 | 0 | 0 | 0 | 79 | 0 |

TABLE 3E

| San | First Amine | | | | | | | |
|---|---|---|---|---|---|---|---|---|
| Second Amine | 1 | 2 | 3 | 4 | 5 | 6 | 7 | 8 |
| 9 | 10 | 10 | 0 | 0 | 0 | 0 | 159 | 63 |
| 10 | 0 | 63 | 0 | 10 | 0 | 0 | 159 | 10 |
| 11 | 10 | 243 | 159 | 113 | 63 | 10 | 202 | 63 |
| 12 | 159 | 316 | 281 | 202 | 202 | 63 | 316 | 281 |
| 13 | 113 | 349 | 316 | 159 | 243 | 113 | 437 | 281 |
| 14 | 63 | 281 | 202 | 202 | 243 | 202 | 409 | 281 |
| 15 | 113 | 316 | 243 | 159 | 409 | 63 | 511 | 380 |
| 16 | 0 | 63 | 0 | 10 | 10 | 0 | 63 | 10 |

Nature of amines ($Y_1$, $Y_2$ and $Y_3$)

The amines selected for the synthesis of 3D libraries may be primary, secondary, aliphatic, aromatic, heterocyclic, aryl, chiral, charged or any combination of these. Reaction conditions may vary with the solubility of the selected amine. Water, 50% DMF and neat DMF are solvents of choice. All amines obtained as hydrochloride salts or containing a carboxylate moiety are neutralised with the required molar quantity of NaOH before the reaction.

An example of a hydrophilic ligand generated in the 3D library above is represented by Formula XIV.

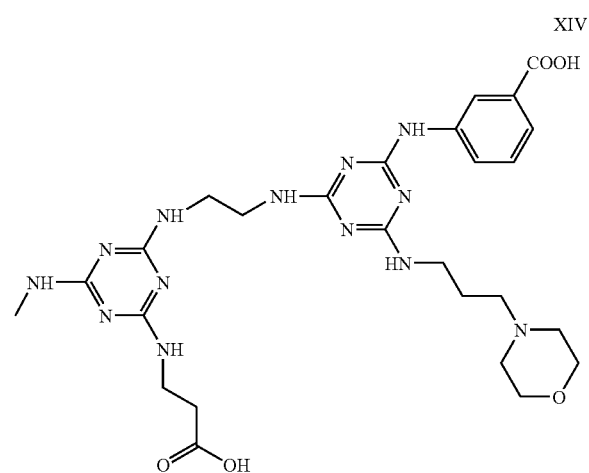

XIV

In this case, $X_1$ is derived from ammonia; $Y_1$ is derived from β-alanine; $X_2$ is derived from 1,2-diaminoethane; $Y_2$ is derived from 3-aminobenzoic acid; and $Y_3$ is derived from 1-(3-aminopropyl)morpholine.

EXAMPLE 8

This Example illustrates the use of another 3-D ligand, that has been found to be especially useful for the isolation and purification of monoclonal antibodies from cell culture broth and polyclonal antibodies from plasma and plasma fractions. It is represented by formula XV In this case, $X_1$ is derived from 1,2-diaminoethane; $Y_1$ is derived from β-alanine; $X_2$ is derived from 1,2-diaminoethane; $Y_2$ is derived from 2-aminophenol; and $Y_3$ is derived from 3-aminophenol.

In this Example, the adsorbent shown in formula XV is used for the purification of Immunoglobulin G from CEA (Clarified Extract A from precipitate A obtained from plasma by the Kistler/Nitschmann method). Adsorbent (loaded at 22 mmol/g onto agarose) was packed into a glass column (10 mL), equilibrated with 10 column volumes of 25 mM sodium phosphate pH 7.0, and loaded with CEA (containing ~400 mg of Immunoglobulin G). The column was then washed with 25 mM sodium phosphate pH 7.0 (5 column volumes), followed by 5 column volumes of 10 mM sodium phosphate (equilibrated to pH 6.5 with citric acid). Bound protein was eluted with 10 mM sodium citrate pH 3.0, followed by 50 mM citric acid. After use, the column was sanitised with 10 column volumes of 0.5 M sodium hydroxide.

The binding capacity of this adsorbent was found to be 43.2 mg/mL, and the elution capacity (total protein eluted in the two elution fractions) found to be 32.8 mg/mL. The first elution contained IgG in approximately 95% purity and an elution capacity of 27 mg/mL of adsorbent.

EXAMPLE 9

This Example illustrates the combinatorial synthesis of a 'library of libraries' using amines grouped into four broad amine classes, aromatic, hydrophobic, positive, and polar. Each of twelve libraries was synthesised in identical fashion to the library described in Examples 1-7, using amines $Y_1$, $Y_2$, and $Y_3$ of classes detailed in Table 4.

TABLE 4

| Number | $Y_1$ | $Y_2$ | $Y_3$ |
|---|---|---|---|
| 1 | Hydrophobic | Aromatic | Aromatic |
| 2 | Hydrophobic | Aromatic | Aromatic |
| 3 | Positive | Aromatic | Aromatic |
| 4 | Positive | Aromatic | Aromatic |

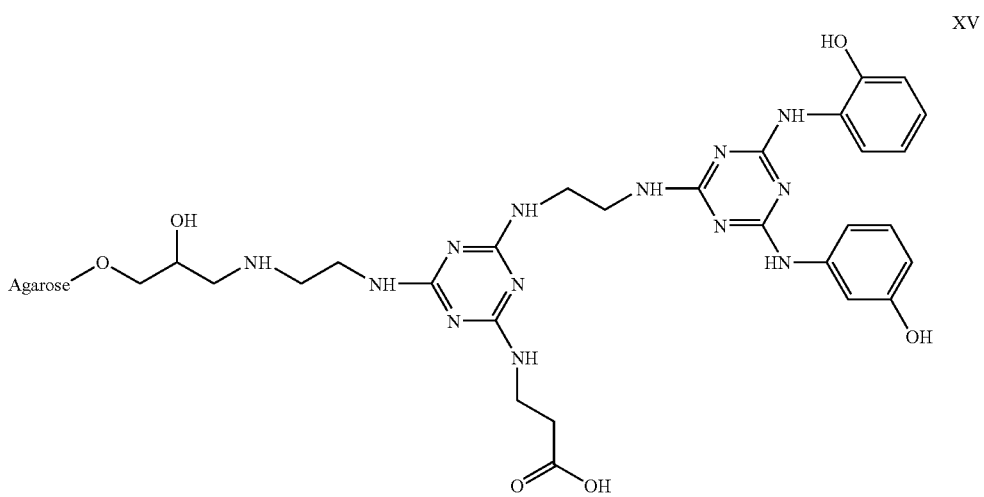

XV

TABLE 4-continued

| Number | $Y_1$ | $Y_2$ | $Y_3$ |
|---|---|---|---|
| 5 | Polar | Hydrophobic | Hydrophobic |
| 6 | Polar | Aromatic | Hydrophobic |
| 7 | Polar | Hydrophobic | Hydrophobic |
| 8 | Polar | Aromatic | Hydrophobic |
| 9 | Positive | Aromatic | Aromatic |
| 10 | Positive | Hydrophobic | Aromatic |
| 11 | Hydrophobic | Aromatic | Aromatic |
| 12 | Hydrophobic | Hydrophobic | Aromatic |

For each library, an identical first amine $Y_1$ was added to all 64 library members, the remaining amines $Y_2$ and $Y_3$, added after spacer arm and triazine addition (as described in previous examples), describing the 64 different gels which comprise each library. Chloride release and TNBS assays were performed at each stage of the solid phase synthesis as described in previous examples.

The amines $Y_1$, $Y_2$, and $Y_3$ for each of the libraries 1-12 are shown (Table 5).

TABLE 5

| Library | $Y_1$ | $Y_2$ | $Y_3$ |
|---|---|---|---|
| 1 | 28 | 4, 5, 14, 18, 19, 26, 29, 30 | 4, 5, 14, 18, 19, 26, 29, 30 |
| 2 | 28 | 4, 5, 14, 18, 19, 26, 29, 30 | 6, 9, 13, 19, 23, 25, 31, 34 |
| 3 | 7 | 1, 4, 5, 14, 18, 19, 29, 30 | 1, 4, 5, 14, 18, 19, 29, 30 |
| 4 | 7 | 1, 4, 5, 14, 18, 19, 29, 30 | 2, 3, 6, 7, 9, 25, 31, 34 |
| 5 | 24 | 15, 16, 17, 20, 27, 28, 32, 36 | 15, 16, 17, 20, 27, 28, 32, 36 |
| 6 | 24 | 15, 16, 17, 20, 27, 28, 32, 36 | 4, 11, 12, 14, 21, 22, 18, 33 |
| 7 | 35 | 15, 16, 17, 20, 27, 28, 32, 36 | 15, 16, 17, 20, 27, 28, 32, 36 |
| 8 | 35 | 15, 16, 17, 20, 27, 28, 32, 36 | 4, 11, 12, 14, 21, 22, 18, 33 |
| 9 | 8 | 1, 4, 5, 14, 18, 19, 29, 30 | 1, 4, 5, 14, 18, 19, 29, 30 |
| 10 | 8 | 1, 4, 5, 14, 18, 19, 29, 30 | 6, 7, 9, 10, 11, 25, 31, 34 |
| 11 | 16 | 1, 4, 5, 14, 18, 19, 29, 30 | 1, 4, 5, 14, 18, 19, 29, 30 |
| 12 | 16 | 1, 4, 5, 14, 18, 19, 29, 30 | 6, 7, 9, 10, 11, 25, 31, 34 | where the numbered amines are as follows:
1 = Aniline;
2 = 2-Aminophenol;
3 = 4-Aminophenol;
4 = m-Toluidine;
5 = 4-Amino-1-benzylpiperidine;
6 = 2-(2-Aminoethyl)-1-methylpyrrolidine;
7 = 1-(2-Aminoethyl)piperidine;
8 = 2-(2-Aminoethyl)pyridine;
9 = 1-(2-Aminoethyl)-pyrrolidine;
10 = 4-(Aminomethyl)piperidine;
11 = (+/−)-2-Aminonorbornane;
12 = 3-Aminobenzyl alcohol;
13 = 4-Amino-1-naphthol;
14 = Phenethylamine;
15 = Butylamine;
16 = Isobutylamine;
17 = (+/−)-sec-Butylamine;
18 = Benzylamine;
19 = Tryptamine;
20 = N-Methyl isopropylamine;
21 = 4-Methyl benzylamine;
22 = 2-(p-Tolyl) ethylamine;
23 = 4-Amino-m-cresol;
24 = 3-Aminobenzamide;
25 = 1-Aminoindane;
26 = N,N-Dimethyl-1,3-phenylenediamine;
27 = 2-Amino-6-methylheptane;
28 = 2-Amino-5-methylhexane;
29 = 3-Amino-1-phenyl butane;
30 = (S)-(−)-1-(1-Naphthyl)ethylamine;
31 = (S)-1,2,3,4-Tetrahydro-1-naphthylamine;
32 = (S)-(+)-3-Methyl-2-butylamine;
33 = 2-Methylbenzylamine;
34 = (S)-(−)-Prolinol;
35 = L-Alanineamide;
36 = 3-Isopropoxypropylamine.

An exemplary 3-D structure from the 'Library of Libraries' synthesis described in Example 9, is:

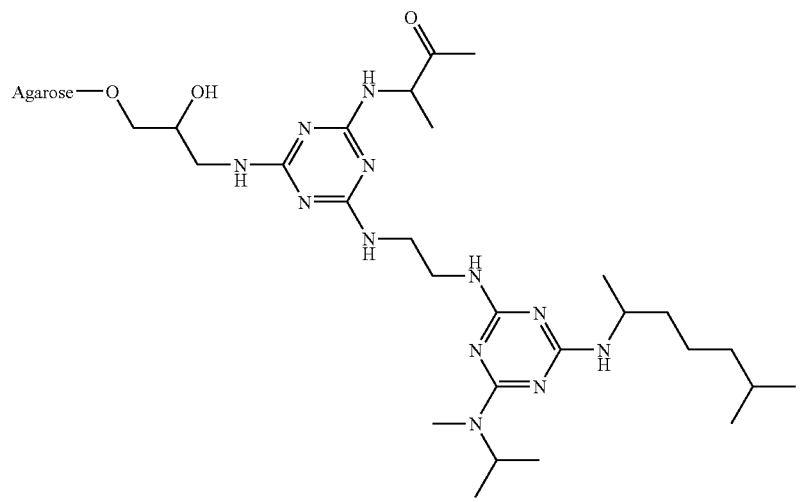

EXAMPLE 10

This Example describes the use of the 'library of libraries', the synthesis of which is described in Example 9, in a screen for binding of the protein alpha-1-antitrypsin (also known as alpha-1-proteinase inhibitor) from a preparation of Cohn IV-I paste. The Cohn IV-I paste was prepared by dissolving paste frozen at 80° C. (20 g) in 15 mM sodium phosphate buffer pH 8.1 (300 mL) in a water bath overnight at 25° C. with continual stirring. This mixture was then centrifuged at 25° C. at 15,000 rpm over 15 minutes, before filtration through 1.0 mm and 0.45 mm filters. The ethanol preservative was washed out of each position in each library by adding 4×0.5 mL portions of 10 mM Tris, 20 mM sodium citrate, 150 mM sodium chloride pH 7.5 to the top of the gel bed. Each portion was allowed to run through under gravity to displace the 20% ethanol preservative in the gel. The bottom of each library component was then sealed before a preparation of Cohn IV-I paste (0.25 mL) was added to the top of each gel bed and mixed with the equilibrated gel. The library was then incubated with the Cohn IV-I load for 30 minutes. After this time the library was uncapped, and the flow through (FT) from each library component was collected separately. Each gel bed was then washed to-remove unbound protein using 3×0.25 mL portions of 10 mM Tris, 20 mM sodium citrate, 150 mM sodium chloride pH 7.5. The wash fraction (W) that was collected from each library component was collected separately. In a single elution step 8 M urea, 25 mM Tris, 150 mM sodium chloride pH 7.5 (3×0.25 mL) was added to the top of each gel bed, and the elution (E) from each library component was collected separately. Finally, a sanitisation (San) step (designed to remove any residual bound material on the gel), comprising 1 mL of 0.2 M sodium hydroxide/30% isopropanol, was added to the top of each gel bed, allowed to run through under gravity and collected separately. The FT and E fractions from each library component were then run on SDS PAGE gels, and analysed by eye for depletion of alpha-1-antitrypsin in the FT fraction, and appearance of alpha-1-antitrypsin in the E fraction. The presence or depletion of alpha-1-antitrypsin in fractions from promising candidates was also confirmed by nephelometry.

EXAMPLE 11

From the 768 individual library components screened, four were chosen to be synthesised individually on a 30 mL scale, using identical chemistry and assays as described for library synthesis in Examples 1-7. The amine composition ($Y_1$, $Y_2$, $Y_3$) of these four resins is shown in Table 6. The amine numbers are as for Table 5.

TABLE 6

| Resin | Amine ($Y_1$) | $Y_2$ | $Y_3$ |
|---|---|---|---|
| A | 7 | 4 | 9 |
| B | 24 | 28 | 36 |
| C | 35 | 27 | 20 |
| D | 35 | 16 | 11 |

These four resins were assessed as follows:

Columns of approximately 10 mL volume and 12 cm height (see Table 7 for details) were equilibrated using 4 column volumes of 10 mM Tris, 20 mM sodium citrate, 150 mM sodium chloride pH 7.5. Cohn IV-I paste, prepared as described in Example 9 (volume see Table 7), was introduced to the column at a flow rate of 50 cmh$^{-1}$. After loading, non-bound protein was washed off the column using 4 column volumes of 10 mM Tris, 20 mM sodium citrate, 150 mM sodium chloride pH 7.5 at 200 cmh$^{-1}$. Two elutions were employed: the first 4 column volumes of 100 mM sodium phosphate, 20 mM sodium citrate, pH 6.1, and the second 4 column volumes of 8 M urea, 25 mM Tris, 150 mM sodium chloride pH 7.5. Each was run at a flow rate of 200 cmh$^{-1}$.

TABLE 7

| | Vol (mL) | Height (cm) | Volume Added (mL) | Volume Equi, Wash, E1, E2, |
|---|---|---|---|---|
| A | 9.5 | 12.2 | 48 | 4 CV |
| B | 10.7 | 13.5 | 51 | 4 CV |
| C | 11.0 | 13.9 | 53 | 4 CV |
| D | 9.0 | 11.4 | 45 | 4 CV |

Non-bound (FT) and elution (E1 and E2) fractions were assayed for alpha-1-antitrypsin by nephelometry. The results are shown, along with calculated binding capacities (BC) and elution capacities (EC) for these materials under these conditions in Table 8.

TABLE 8

| | Load (mg) | NB (mg) | E1 (mg) | E2 (mg) | BC (mg/mL) | EC (mg/mL) | BC (%) | EC (%) |
|---|---|---|---|---|---|---|---|---|
| A | 221.0 | 108 | 0 | 25.0 | 11.8 | 2.6 | 52 | 11 |
| B | 244.8 | 111 | 0 | 53.3 | 12.5 | 5.0 | 55 | 22 |
| C | 245.4 | 87.4 | 0 | 81.8 | 14.4 | 7.4 | 64 | 33 |
| D | 202.5 | 148 | 0 | 6.83 | 6.1 | 0.8 | 27 | 3 |

EXAMPLE 12

This Example describes the synthesis of a 'four-dimensional' library, comprising 3 triazine groups and 4 independently variable Y groups. PuraBead support matrix was epoxide-activated as described in Example 1 to a final epoxide loading of 5.6 mmol/g settled gel, then Spacer $X_1$ incorporated by treatment of the epoxide resin with ethylenediamine in an analogous fashion to the spacer addition described in Example 5.

This resin was reacted with trichlorotriazine as described in Example 3 to generate a dichlorotriazine gel. The chloride level was assayed and found to be 12.5 mmol/g settled gel.

First amine $Y_1$ (structure XI) was added by addition of a solution of tryptamine to the dichlorotriazine in an analogous fashion to the amine addition described in Example 4. The chloride level was 5.4 mmol/g settled gel.

Spacer $X_2$ (structure XI) was incorporated by addition of a solution of ethylenediamine in an analogous fashion to the spacer addition described in Example 5. A TNBS assay showed the amine level to be 5.4 mmol/g settled gel.

A second addition of trichlorotriazine was then accomplished using analogous conditions to that of the first (see above). The chloride level was 12.1 mmol/g settled gel.

Second amine $Y_2$ (structure XI) was added by addition of a solution of tyramine to the dichlorotriazine in an analogous fashion to the amine addition described in Example 4. The chloride level was 12.1 mmol/g settled gel.

Spacer $X_3$ (structure XI) was incorporated by addition of 0.88 ammonia in an analogous fashion to the spacer addition described in Example 2. A TNBS assay on the material generated was performed (5.7 mmol/g settled gel).

A third addition of trichlorotriazine was then accomplished using conditions analogous to the first two. The chloride level was 12.5 µmol/g settled gel.

The bis-chloro-bis-triazine gel obtained from the previous step was weighed into eight bottles and reacted with eight different amines in an analogous fashion to that described in Example 6, thus incorporating amine $Y_3$ (structure XI). Chloride release figures (µmol/g settled gel) for these additions are shown in Table 9.

TABLE 9

| Column Index in Final Library | Intermediate Amine $Y_3$ | Chloride Release |
|---|---|---|
| 1 | B-alanine | 8.0 |
| 2 | 3-aminophenol | 8.0 |
| 3 | 3-aminobenzyl alcohol | 8.0 |
| 4 | tyramine | 8.0 |
| 5 | isobutylamine | 8.0 |
| 6 | benzylamine | 8.0 |

TABLE 9-continued

| Column Index in Final Library | Intermediate Amine $Y_3$ | Chloride Release |
|---|---|---|
| 7 | tryptamine | 9.0 |
| 8 | 2-ethylthio(ethylamine) | 0.0 |

After addition of intermediate amines shown above, each of the eight gels was slurried and distributed down a row of eight wells as described in Example 7. Eight different amines $Y_4$ were then added across the eight rows to generate a total of 64 different quadruply amine-substituted resins. The results in Table 10 show the chloride release data obtained after this final substitution $Y_4$ as mmol chloride released per g gel.

TABLE 10

| | 1 | 2 | 3 | 4 | 5 | 6 | 7 | 8 |
|---|---|---|---|---|---|---|---|---|
| β-alanine | 4.4 | 7.1 | 6.0 | 6.3 | 4.4 | 9.9 | 5.9 | 7.3 |
| 3-aminophenol | 4.4 | 6.6 | 6.2 | 7.6 | 6.4 | 3.9 | 6.7 | 8.1 |
| 3-aminobenzyl alcohol | 4.6 | 7.2 | 7.1 | 7.1 | 5.7 | 4.0 | 6.6 | 8.4 |
| tyramine | 5.1 | 6.6 | 7.1 | 4.6 | 6.9 | 6.1 | 7.5 | 8.3 |
| isobutylamine | 4.2 | 5.1 | 6.4 | 4.7 | 4.8 | 3.4 | 3.7 | 4.9 |
| benzylamine | 4.8 | 4.2 | 6.1 | 5.7 | 6.9 | 6.9 | 5.7 | 7.5 |
| tryptamine | 4.5 | 7.0 | 4.6 | 7.0 | 7.1 | 3.2 | 7.7 | 8.5 |
| 2-ethylthio-(ethylamine) | 16.1 | 16.5 | 21.0 | 16.0 | 15.1 | 14.6 | 14.4 | 14.9 |

An exemplary 4-D structure is:

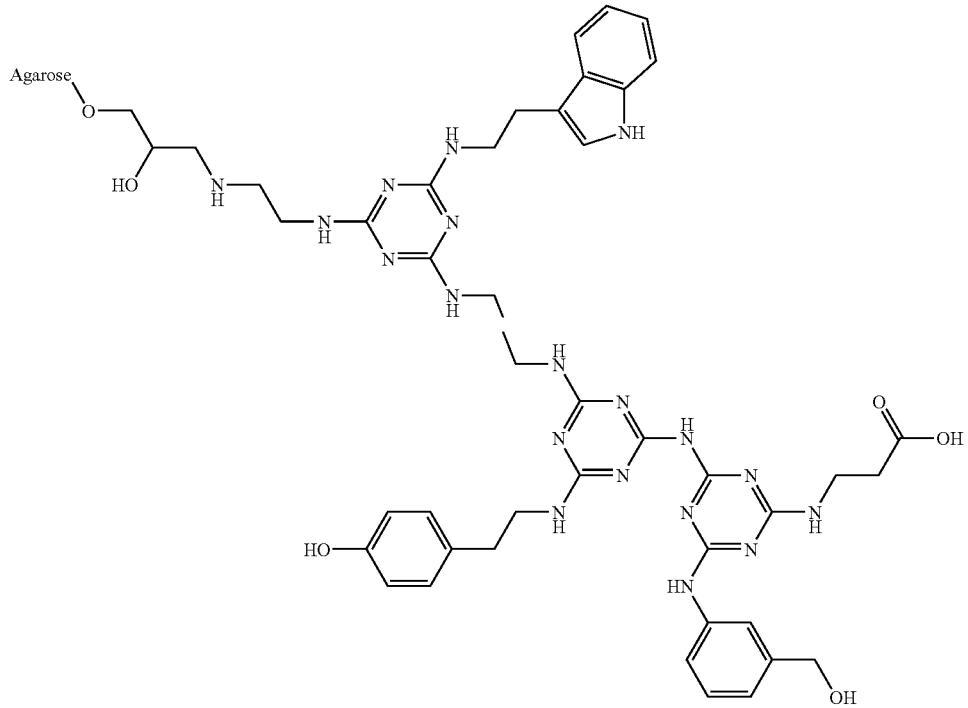

The invention claimed is:

1. A compound comprising affinity ligands wherein the compound is immobilized on a support matrix, and wherein the compound, together with the support matrix, is represented by the formula

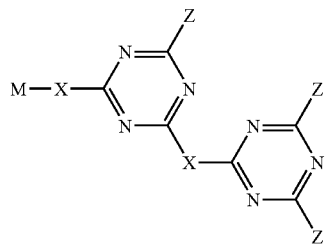

wherein each Z is the same or different and is

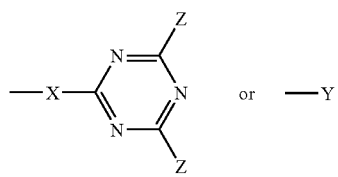

wherein each X is independently selected from —NH— and diaminoalkane, diethylenetriamine or tris(aminoethyl)amine spacers linked to the triazine rings by amine groups,
each Y is independently selected from optionally substituted aliphatic and aromatic primary amines, and the Y groups provide the affinity ligands; and
M is a support matrix.

2. The compound according to claim 1, of the formula

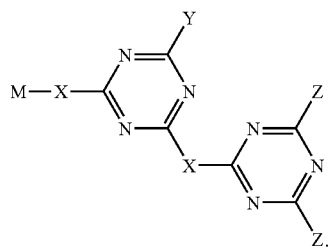

3. The compound according to claim 2, wherein either or each Z is Y.

4. The compound according to claim 1, wherein each X independently represents a secondary amino group or a diaminoalkane.

5. The compound according to claim 1, of the formula

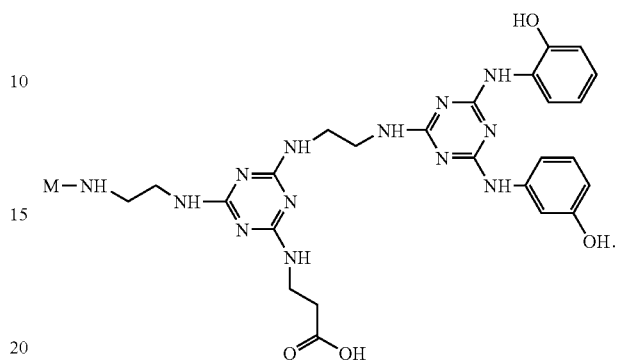

6. A method for the synthesis of a compound comprising affinity ligands wherein the compound is immobilized on a support matrix, and wherein the compound, together with the support matrix, is represented by the formula

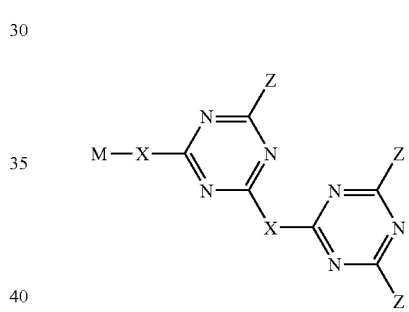

wherein each Z is the same or different and is

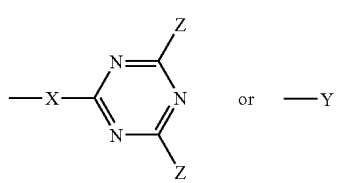

wherein each X is independently selected from —NH— and diaminoalkane, diethylenetriamine or tris(aminoethyl)amine spacers linked to the triazine rings by amine groups;
each Y is independently selected from optionally substituted aliphatic and aromatic primary amines, and the Y groups provide the affinity ligands; and
M is a support matrix:
wherein said method comprises the reaction of a compound of the formula

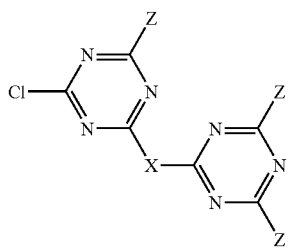

wherein each Z is the same or different and is

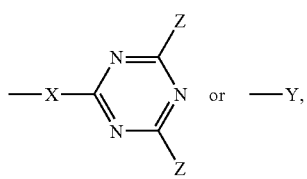

with an amine-containing support matrix.

7. A library of compounds of the formula:

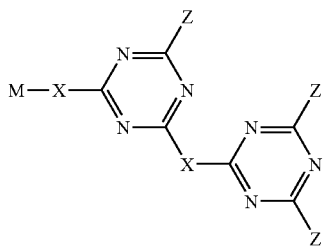

wherein each Z is the same or different and is

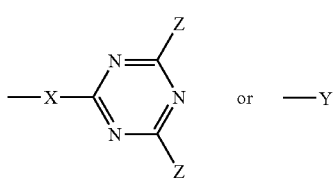

wherein each X is independently selected from —NH— and diaminoalkane, diethylenetriamine or tris(aminoethyl)amine spacers linked to the triazine rings by amine groups;

each Y is independently selected from optionally substituted aliphatic and aromatic primary amines, and the Y groups provide the affinity ligands; and M is a support matrix.

8. A method for the production of a library of compounds of the formula:

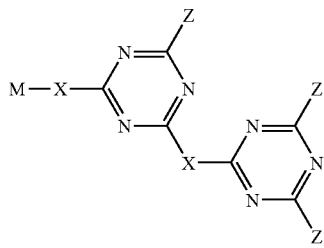

wherein each Z is the same or different and is

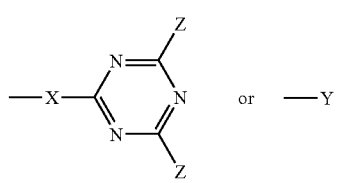

wherein each X is independently selected from —NH— and diaminoalkane, diethylenetriamine or tris(aminoethyl)amine spacers linked to the triazine rings by amine groups; each Y is independently selected from optionally substituted aliphatic and aromatic primary amines, and the Y groups provide the affinity ligands; and M is a support matrix;

wherein said method comprises the synthesis of intermediate structures, either singly or in multiples, dividing the structures into smaller portions, and carrying out appropriate subsequent reaction steps.

9. A method for the separation, isolation, and/or purification of peptides and proteins from a preparation of biological or pharmaceutical compound wherein said method comprises the use of a compound of the formula

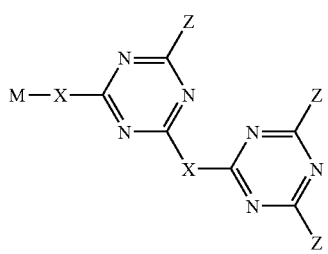

wherein each Z is the same or different and is

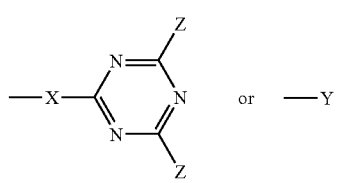

wherein each X is independently selected from —NH— and diaminoalkane, diethylenetriamine or tris(aminoethyl)amine spacers linked to the triazine rings by amine groups;

each Y is independently selected from optionally substituted aliphatic and aromatic primary amines, and the Y groups provide the affinity ligands; and M is a support matrix.

10. The method, according to claim 9, which comprises subjecting a sample containing a proteinaceous material to affinity chromatography using said compound.

11. The process according to claim 10, wherein the proteinaceous material is an immunoglobulin or a subclass, fragment, precursor or derivative thereof, including fusion proteins, whether derived from natural or recombinant sources.

12. The method according to claim 9, for the removal of contaminants, including toxic or pathogenic entities, from a preparation of biological or pharmaceutical compound.

13. The library, according to claim 7, wherein the compounds are on a common support.

14. The compound according to claim 1, which contains 2 or more triazine rings and 3 independently available Y groups.

15. The compound according to claim 1, which contains 3 or more triazine rings and 4 independently available Y groups.

* * * * *